(12) United States Patent
Badros et al.

(10) Patent No.: US 11,147,970 B2
(45) Date of Patent: Oct. 19, 2021

(54) PERSONALIZED NETWORK SEARCHING

(71) Applicant: Google LLC, Mountain View, CA (US)

(72) Inventors: Gregory Joseph Badros, Palo Alto, CA (US); Stephen Lawrence, Palo Alto, CA (US)

(73) Assignee: Google LLC, Mountain View, CA (US)

( * ) Notice: Subject to any disclaimer, the term of this patent is extended or adjusted under 35 U.S.C. 154(b) by 0 days.

(21) Appl. No.: 16/186,129

(22) Filed: Nov. 9, 2018

(65) Prior Publication Data

US 2019/0080013 A1 Mar. 14, 2019

Related U.S. Application Data

(63) Continuation of application No. 15/854,208, filed on Dec. 26, 2017, now Pat. No. 10,140,375, which is a
(Continued)

(51) Int. Cl.
*G06F 16/00* (2019.01)
*A61N 1/36* (2006.01)
(Continued)

(52) U.S. Cl.
CPC ..... *A61N 1/36071* (2013.01); *A61N 1/36003* (2013.01); *A61N 1/36017* (2013.01);
(Continued)

(58) Field of Classification Search
CPC .............. G06F 16/9535; G06F 16/972; G06Q 30/0241; G06Q 30/0201; Y10S 707/99933; Y10S 707/99943; Y10S 707/99945
See application file for complete search history.

(56) References Cited

U.S. PATENT DOCUMENTS 4,554,417 A 11/1985 Boyer
5,724,521 A 3/1998 Dedrick
(Continued)

FOREIGN PATENT DOCUMENTS

GB 2 367 925 A 4/2002
JP 2002-258874 A 9/2002
(Continued)

OTHER PUBLICATIONS

Communication pursuant to Article 94(3) EPC for EP Appl. Ser. No. 18167072.0 dated May 3, 2019 (6 pages).
(Continued)

*Primary Examiner* — Cheryl Lewis
(74) *Attorney, Agent, or Firm* — Middleton Reutlinger

(57) ABSTRACT

Personalized network searching, in which a search query is received from a user, and a request is received to personalize a search result. Responsive to the search query and the request to personalize the search result, a personalized search result is generated by searching a personalized search object. Responsive to the search query, a general search result is generated by searching the general search object. The personalized search result and the general search result are provided to a client device, an advertisement is selected based at least in part upon the personalized search object, and the advertisement, the personalized search result, and the general search result are displayed.

20 Claims, 4 Drawing Sheets

Related U.S. Application Data continuation of application No. 15/492,513, filed on Apr. 20, 2017, now Pat. No. 10,398,898, which is a continuation of application No. 14/516,019, filed on Oct. 16, 2014, now Pat. No. 9,679,067, which is a continuation of application No. 14/074,872, filed on Nov. 8, 2013, now Pat. No. 8,886,626, which is a continuation of application No. 13/442,386, filed on Apr. 9, 2012, now Pat. No. 8,612,415, which is a continuation of application No. 13/172,961, filed on Jun. 30, 2011, now Pat. No. 8,166,017, which is a continuation of application No. 12/099,583, filed on Apr. 8, 2008, now Pat. No. 8,015,170, which is a continuation of application No. 10/726,410, filed on Dec. 3, 2003, now Pat. No. 7,523,096.

(51) Int. Cl.
  *G06F 16/9535* (2019.01)
  *G06F 16/958* (2019.01)
  *G06Q 30/02* (2012.01)

(52) U.S. Cl.
  CPC ..... *A61N 1/36021* (2013.01); *A61N 1/36057* (2013.01); *G06F 16/9535* (2019.01); *G06F 16/972* (2019.01); *G06Q 30/0201* (2013.01); *G06Q 30/0241* (2013.01); *Y10S 707/99933* (2013.01); *Y10S 707/99943* (2013.01); *Y10S 707/99945* (2013.01)

(56) References Cited

U.S. PATENT DOCUMENTS

| | | | |
|---|---|---|---|
| 5,740,549 A | 4/1998 | Reilly et al. |
| 5,790,426 A | 8/1998 | Robinson |
| 5,848,397 A | 12/1998 | Marsh et al. |
| 5,884,282 A | 3/1999 | Robinson |
| 5,948,061 A | 9/1999 | Merriman et al. |
| 6,023,708 A | 2/2000 | Mendez et al. |
| 6,026,368 A | 2/2000 | Brown et al. |
| 6,044,376 A | 3/2000 | Kurtzman, II |
| 6,078,914 A | 6/2000 | Redfern |
| 6,101,491 A | 8/2000 | Woods |
| 6,108,493 A | 8/2000 | Miller et al. |
| 6,144,944 A | 11/2000 | Kurtzman et al. |
| 6,167,382 A | 12/2000 | Sparks et al. |
| 6,182,068 B1 | 1/2001 | Culliss |
| 6,266,649 B1 | 7/2001 | Linden et al. |
| 6,269,361 B1 | 7/2001 | Davis et al. |
| 6,401,075 B1 | 6/2002 | Mason et al. |
| 6,408,316 B1 * | 6/2002 | Himmel .............. G06F 16/9562 715/206 |
| 6,480,837 B1 | 11/2002 | Dutta |
| 6,480,853 B1 | 11/2002 | Jain |
| 6,493,702 B1 | 12/2002 | Adar et al. |
| 6,557,028 B2 * | 4/2003 | Cragun .............. G06F 16/9562 709/205 |
| 6,560,640 B2 | 5/2003 | Smethers |
| 6,601,061 B1 | 7/2003 | Holt et al. |
| 6,615,237 B1 | 9/2003 | Kyne et al. |
| 6,615,247 B1 | 9/2003 | Murphy |
| 6,624,750 B1 | 9/2003 | Marman et al. |
| 6,725,227 B1 | 4/2004 | Li |
| 6,732,088 B1 | 5/2004 | Glance |
| 6,754,188 B1 | 6/2004 | Garahi et al. |
| 6,904,146 B2 | 6/2005 | Domer et al. |
| 6,950,861 B1 | 9/2005 | Amro et al. |
| 6,963,867 B2 | 11/2005 | Ford et al. |
| 6,981,040 B1 | 12/2005 | Konig et al. |
| 6,985,882 B1 | 1/2006 | Del Sesto |
| 7,003,099 B1 | 2/2006 | Zhang et al. |
| 7,020,501 B1 | 3/2006 | Elliott et al. |
| 7,027,773 B1 | 4/2006 | McMillin |
| 7,031,961 B2 | 4/2006 | Pitkow et al. |
| 7,039,599 B2 | 5/2006 | Merriman et al. |
| 7,136,875 B2 | 11/2006 | Anderson et al. |
| 7,359,504 B1 | 4/2008 | Reuss et al. |
| 7,421,257 B1 | 9/2008 | Elliott |
| 7,523,096 B2 | 4/2009 | Badros et al. |
| 7,624,337 B2 | 11/2009 | Sull et al. |
| 7,647,312 B2 | 1/2010 | Dai |
| 7,664,669 B1 | 2/2010 | Adams et al. |
| 7,725,422 B2 | 5/2010 | Ryan et al. |
| 7,734,850 B2 | 6/2010 | Graham |
| 7,756,753 B1 | 7/2010 | McFarland |
| 7,933,917 B2 | 4/2011 | Kim et al. |
| 7,987,294 B2 | 7/2011 | Bryce et al. |
| 7,995,899 B2 | 8/2011 | Heredia et al. |
| 8,015,170 B2 | 9/2011 | Badros et al. |
| 8,166,017 B2 | 4/2012 | Badros et al. |
| 8,433,995 B1 | 4/2013 | Karam |
| 8,612,415 B2 | 12/2013 | Badros et al. |
| 8,886,626 B2 | 11/2014 | Badros et al. |
| 9,679,067 B2 | 6/2017 | Badros et al. |
| 10,140,375 B2 | 11/2018 | Badros et al. |
| 10,398,898 B2 | 9/2019 | Badros et al. |
| 10,588,139 B2 | 3/2020 | Elliott et al. |
| 2001/0037332 A1 | 11/2001 | Miller et al. |
| 2002/0166047 A1 | 11/2002 | Kawamoto |
| 2002/0174354 A1 | 11/2002 | Bel et al. |
| 2002/0198962 A1 | 12/2002 | Horn et al. |
| 2003/0069874 A1 | 4/2003 | Hertzog et al. |
| 2003/0073412 A1 | 4/2003 | Meade, II |
| 2003/0088554 A1 | 5/2003 | Ryan et al. |
| 2003/0101216 A1 * | 5/2003 | Gupta ................. G06F 16/9562 709/203 |
| 2003/0103088 A1 | 6/2003 | Dresti et al. |
| 2004/0002938 A1 | 1/2004 | Deguchi |
| 2004/0107236 A1 | 6/2004 | Nakagawa et al. |
| 2005/0055335 A1 | 3/2005 | Bae et al. |
| 2005/0091205 A1 | 4/2005 | Sidlosky et al. |
| 2005/0097623 A1 | 5/2005 | Tecot et al. |
| 2006/0015405 A1 | 1/2006 | Bala et al. |
| 2006/0120433 A1 | 6/2006 | Baker et al. |
| 2006/0235873 A1 | 10/2006 | Thomas |
| 2007/0112734 A1 | 5/2007 | Xin et al. |
| 2009/0249224 A1 | 10/2009 | Davis et al. |

FOREIGN PATENT DOCUMENTS

| | | |
|---|---|---|
| JP | 2003-203088 A | 7/2003 |
| WO | WO-97/21183 A | 6/1997 |
| WO | WO-98/12881 A | 3/1998 |
| WO | WO-01/16807 A1 | 3/2001 |
| WO | WO-01/035211 A3 | 5/2001 |
| WO | WO-01/55909 A1 | 8/2001 |
| WO | WO-01/67313 A1 | 9/2001 |
| WO | WO-02/15617 A1 | 2/2002 |
| WO | WO-02/057865 | 7/2002 |
| WO | WO-03/036520 A1 | 5/2003 |

OTHER PUBLICATIONS

US Notice of Allowance for U.S. Appl. No. 15/492,513 dated Apr. 19, 2019 (5 pages).
US Notice of Allowance for U.S. Appl. No. 15/492,513 dated Feb. 27, 2019 (10 pages).
U.S. Appl. No. 95/001,061, filed Sep. 3, 2002, Reexamination of Stone et al.
U.S. Appl. No. 95/001,069, filed Jul. 11, 2002, Reexamination of Dean et al.
U.S. Appl. No. 95/001,073, filed Sep. 30, 2004, Reexamination of Stone et al.
A9.com, "What's New & Cool", web page at http://a9.com/-/company/whatsCool.jsp as available via the Internet and printed on Jul. 29, 2004.
AdForce, Inc., A Complete Guide to AdForce, Version 2.6, 1998.
AdFroce, Inc., S-1/A SEC Filing. May 6, 1999.
AdKnowledge Campaign Manager: Reviewer's Guide, AdKnowledge, Aug. 1998.

(56) References Cited

OTHER PUBLICATIONS

AdKnowledge Market March Planner: Reviewer's Guide, AdKnowledge, May 1998.
Ad-Star.com website archive from www.Archive.org, Apr. 12, 1997 and Feb. 1, 1997.
Barrett, R. et al., "How to Personalize the Web", Proceedings of the ACM Conference on Human Factors in Computing Systems, Atlanta, GA, 1997.
Baseview Products, Inc., AdManagerPro Administation Manual v. 2,0, Dec. 1998.
Baseview Products, Inc., ClessMenagarPro Administration Manual v. 1.0.5, Feb. 1, 1997.
Bharat,Krishna, "SearchPad: Explicit Capture of Search Context to Support Web Search", Ninth World Wide Web Conference, Amsterdam, May 15-19, 2000, pp. 1-13.
Bk2site, "Now any yahoo can be a Yahoo!", web page at http://bk2site.sourceforge.net/, as available via the Internet and printed on Sep. 28, 2003.
BlinkPro, "BlinkPro: Powerful Bookmark Manager", web page at http://www.blinkpro.com/, as available via the Internet and printed on Sep. 28, 2003.
Bookmark Tracker, "Welcome to the new BookmarkTracker.coml", web page at http://www.bookmarktracker.com/, as available via the Internet and printed on Sep. 28, 2003.
Business Wire, "Global Network, Inc. Enters into Agreement in Principle With Major Advertising Agnecy," Oct. 4, 1999.
Czyzowicz, J. et al., "Evaluation of Hotlink Assignment Heuristics for Improving Web Access," Proceedings of the Second International Conference on Internet Computing (IC'01), Las Vegas, NV, vol. 2, Jun. 25-28, 2001, pp. 793-799.
Decision of Re-Examination for corresponding Chinese Application No. 200400356468, mailed Nov. 25, 2009, with English-language translation (22 pages).
Dedrick, R., A Consumption Model for Targeted Electronic Advertising, Intel Architecture Labs. IEEE, 1995.
Dedrick, R., Interactive Electronic Advertising, IEEE, 1994.
Denoue, Laurent et al., "An annotation tool for Web browsers and its applications to information retrieval", Syscom, Universite de Savole, France, 2000.
EPO Office Action for Appl. Ser. No. 18167072.0 dated Jun. 8, 2018 (5 pages).
EPO Search Report for Appl. Ser. No. 18167072.0 dated May 25, 2011 (5 pages).
Furl, "What is Furl?" web page at http://www.furl.net/learnMore.jsp, as available via the Internet and printed on Jul. 29, 2004.
IKeepBookmarks.com, "A Web Eased Bookmark Manager", web page at http://www.Ikeepbookmarks.com/ as available on the Internet and printed on Sep. 28, 2003.
Information Access Technologies, Inc., Aaddzz brochure, "The Best Way to Buy and Sell Web Advertising Space," © 1997.
Information Access Technologies, Inc., Aaddzz.com website archive from www.Archive.org, archived on Jan. 30, 1998.
International Search Report (Corrected) for PCT Appl. Ser. No. PCT/US2004/039176, dated Feb. 18, 2005 (7 pgs).
Kaasten S. et al., "How People Recognize Previously Seen WWW Pages from Titles, URLs and Thumbnails", In X. Faulkner, J. Finlay, F. Detienne (Eds) People and Computers XVI (Proceedings of Human Computer Interaction 2002). BCS Conference Series. 247-285. Springer Verlag.
Kaastens, S. et al., "Integrating Back, History and Bookmark in Web Bowsers", Extended Abstracts of the ACM Conference of Human Factors in Computing Systems (CHI'01), ACM Press, 2001, pp. 379-380.
Kaasten, S., et al., "Designing an Integrated Bookmark/History System for Web Browsing", History Keeping in Computer Applications: A Workshop. Held at Human-Computer Interaction Laboratory, University of Maryland at College Park, Maryland, USA, Dec. 3, 1999.
Kaasten, Shaun, et al., "Designing an Integrated Bookmark/History System for Web Browsing". Proceedings of the Western Computer Graphics Symposium 2000, Panorama Mountain Village, BC, Canada, Mar. 28-29, 2000.
Kahan, J. et al., "Annotea: An Open RDF infrastructure for Shared Web Annotations", Proceedings from Tenth World Wide Web Conference, Hong Kong, May 1-5, 2001, pp. 1-25.
Maarek. Yoelle S. et al., "Automatically Organizing Bookmarks per Contents", Fifth International World Wide Web Conference, Paris, France, May 6-10, 1996, pp. 1-17.
Middleton, S.E., et al., "Capturing knowledge of user preferences: ontologies on recommender systems", Proceedings of the First International Conference on Knowledge Capture (K-CAP), Victoria, BC, Canada, Oct. 2001.
Notice of Allowance issued in U.S. Appl. No. 10/726,410 dated Dec. 13, 2007, 7 pages.
Office Action for corresponding Chinese Application No. 200400356488, dated Jul. 4, 2008, with English-language translation (11 pages).
Office Action for corresponding Chinese Application No. 200400356468, dated Mar. 21, 2008, with English-language Translation (11 pages).
Office Action for corresponding Chinese Application No. 20100110995.9 dated Dec. 2, 2010, with English Translation (5 pages).
Office Action for corresponding Chinese Application No. 20100110995.9 dated Nov. 9, 2011, with English Translation (5 pages).
Office Action for corresponding EPO application 04811831.9, dated Apr. 30, 2008 (4 pages).
Office Action for corresponding Indian Application No. 1516/KOLNP/2006, dated Jun. 25, 2010 (38 pages).
Office Action for corresponding Israel Appl. Ser. No. 208680, dated May 26, 2011, with English translation (5 pages).
Office Action for U.S. Appl. No. 10/726,410, dated May 31, 2007 (6 pages).
Oztekin, B. Uygar et al., "Usage Meets Link Analysis: Toward Improving Site Specific and Intranet Search via Usage Statistics", Department of Computer Science and Engineering, University of Minnesota, Minneapolis, MN, May 24, 2004, pp. 1-10.
Piwowarski et al., "Predicitive User Click Models Based on Clickthrough History", ACM, Jul. 2011, pp. 1-8.
Request for Reexamination of U.S. Pat. No. 6,446,045 B1, U.S. Appl. No. 95/001,0617 dated Jul. 7, 2008.
Request for Reexamination of U.S. Pat. No. 6,829,587 B2, U.S. Appl. No. 95/001,068, dated Jul. 14, 2008.
Request for Reexamination of U.S. Pat. No. 7,240,025 B2, U.S. Appl. No. 95/001,073, dated Jul. 30, 2008.
Request for Reexamination of U.S. Pat. No. 7,249,059 B2, U.S. Appl. No. 95/001,069, dated Jul. 21, 2008.
Save This, "Getting started with Save This", web page at http://www.savethis.clickability.com/saveThisApp?clickMap=displayHelp&helpID=0, as available via the Internet and printed on Sep. 28, 2003.
Staab, S. et al., "An Annotation Framework for the Semantic Web", Proceedings of the First International Workshop on Multimedia Annotation, Tokyo, Japan, Jan. 30-31, 2001.
Summons to Attend Oral Proceedings Pursuant to Rule 115(1) EPC for EP Application No. 04811831.9 dated Nov. 11, 2017.
Tauschner, Linda et al., "Revisitation Patterns in World Wide Web Navigation". Proceedings of the Conference on Human Factors in Computing Systems, 1997.
Terveen, Loren et al., "Phoaks: A System for Sharing ReEcommendations", Communications of the ACM, vol. 40, No. 3, Mar. 1997, pp. 59-82.
TinyURL.com/ "Welcome to Tiny URLI", web page at http://tinyurl.com/, as available via the Internet and printed on Nov. 11, 2003.
US Final Office Action for U.S. Appl. No. 10/726,410, dated Dec. 13, 2006 (11 pgs).
US Notice of Allowance for U.S. Appl. No. 12/099,583 dated Apr. 29, 2011 (15 pages).
US Notice of Allowance for U.S. Appl. No. 10/726,410, dated Jul. 15, 2008 (8 pages).
US Notice of Allowance for U.S. Appl. No. 13/171,991, dated Nov. 28, 2011 (12 pgs).

(56) References Cited

OTHER PUBLICATIONS

US Notice of Allowance for U.S. Appl. No. 13/442,386, dated Aug. 14, 2013 (10 pgs).
US Notice of Allowance for U.S. Appl. No. 14/074,872, dated Jun. 19, 2014 (16 pgs).
US Notice of Allowance for U.S. Appl. No. 15/854,208 dated Oct. 11, 2018 (9 pages).
US Notice of Allowance for U.S. Appl. No. 13/172,961, dated Dec. 20, 2011 (13 pgs).
US Office Action for U.S. Appl. No. 14/516,019, dated Aug. 25, 2016 (10 pages).
US Office Acton for U.S. Appl. No. 10/726,410, dated Jun. 14, 2006 (9 pgs).
US Office Action for U.S. Appl. No, 12/099,583, dated Oct. 28, 2010 (9 pgs).
US Office Action for U.S. Appl. No. 13/442,386, dated Jun. 7, 2013 (9 pgs).
US Office Action for U.S. Appl. No. 15/854,208 dated Mar. 22, 2018 (21 pages).
W3C, "An Annotea Bookmark Schema", web page at http://www.w3.org/2003/07/Annotea/BookmarkSchema-20030707 as available via the Internet and printed on Sep. 28, 2003.
W3C, "RSS 1.0 channel for bookmark sharing", web page at http://lists.w3org/Archives/Public/www-annotation/2001JanJun/0002.html, as available via the Internet and printed on Sep. 28, 2003.
Washington Post, "Marking a New Tool for Surfers", web page at http://www.washingtonpost.com/ac2/wp-dyn/A132-2000Sep13?language=printer, as available via the Internet and printed on Sep. 29, 2003.
Wen-Syan Li et al., "PowerBookmarks: A System for Personalizable Web Information Organization, Sharing and Management", Sigmod Conference, 1999, pp. 565-567.
Zeff, R. et al., Advertising on the Internet, 2nd Ed., John Wiley & Sons, 1999.
Znail, "For easier living in a virtual world", web page at http://znail.com/, as available via the Internet and printed on Sep. 28, 3003.
Decision to Refuse for EP Appln. Ser. No. 18167072.0 dated May 13, 2020 (12 pages).
First Action Interview Pilot Program Pre-Interview Communication for U.S. Appl. No. 16/186,211 dated Aug. 19, 2020 (6 pages).
Supplemental Notice of Allowance for U.S. Appl. No. 16/186,211 dated Nov. 19, 2020 (2 pages).
U.S. Appl. No. 10/726,410, filed Dec. 3, 2003.
U.S. Appl. No. 12/099,583, filed Apr. 8, 2008.
U.S. Appl. No. 13/172,961, filed Jun. 30, 2011.
U.S. Appl. No. 13/442,386, filed Apr. 9, 2012.
U.S. Appl. No. 14/074,872, filed Nov. 8, 2013.
U.S. Appl. No. 14/516,019, filed Oct. 16, 2014.
U.S. Appl. No. 15/492,513, filed Apr. 20, 2017.
U.S. Appl. No. 15/854,208, filed Dec. 26, 2017.
Non-Final Office Action for U.S. Appl. No. 16/186,168 dated Oct. 30, 2020 (7 pages).
Notice of Allowance for U.S. Appl. No. 16/186,211 dated Sep. 28, 2020 (9 pages).
"Exhibit B-1: Invalidity Claim Chart for Claims 1-11, and 13-20 of U.S. Pat. No. 10,140,375 (the '375 patent') Regarding International Patent Application Pub. No. WO 01/35211 ('Kapoor')", retrieved Dec. 16, 2020 (30 pages).
"Exhibit B-2: Invalidity Claim Chart for Claims 1-11, and 13-20 of U.S. Pat. No. 10,140,375 (the '375 patent') Regarding U.S. Patent Application No. 2001/0037332 ('Miller')", retrieved Dec. 16, 2020 (28 pages).
"Exhibit B-3: Invalidity Claim Chart for Claims 1-11, and 13-20 of U.S. Pat. No. 10,140,375 (the '375 patent') Regarding U.S. Pat. No. 6,480,853 ('Jain')", retrieved Dec. 16, 2020 (26 pages).
"Exhibit B-4: Invalidity Claim Chart for Claims 1-11, and 13-20 of U.S. Pat. No. 10,140,375 (the '375 patent') Regarding U.S. Patent Application Pub. No. 2004/0107236 ('Nakagawa')", retrieved Dec. 16, 2020 (37 pages).
"Exhibit B-5: Invalidity Claim Chart for Claims 1-11, and 13-20 of U.S. Pat. No. 10,140,375 (the '375 patent') Regarding U.S. Pat. No. 6,023,708 ('Mendez')", retrieved Dec. 16, 2020 (35 pages).
"Exhibit B-6: Invalidity Claim Chart for Claims 1-11, and 13-20 of U.S. Pat. No. 10,140,375 (the '375 patent') Regarding U.S. Pat. No. 7,725,422 ('Ryan')", retrieved Dec. 16, 2020 (27 pages).
"Exhibit B-7: Invalidity Claim Chart for Claims 1-11, and 13-20 of U.S. Pat. No. 10,140,375 (the '375 patent') Regarding U.S. Pat. No. 6,493,702 ('Adar')", retrieved Dec. 16, 2020 (28 pages).
"Exhibit B-8: Invalidity Claim Chart for Claims 1-11, and 13-20 of U.S. Pat. No. 10,140,375 (the '375 patent') Regarding U.S. Patent Application Pub. No. 2002/0198962 ('Horn')", retrieved Dec. 16, 2020 (33 pages).
"Exhibit B-9: Invalidity Claim Chart for Claims 1-11, and 13-20 of U.S. Pat. No. 10,140,375 (the '375 patent') Regarding International Patent Application Pub. No. WO 01/55909 ('Lim')", retrieved Dec. 16, 2020 (30 pages).
*Google LLC* v. *Sonos, Inc.*, Defendant Sonos, Inc's Answer and Affirmative Defenses To First Amended Complaint for Patent Infringement, United States District Court, Northern District of California, San Francisco Division, Case 3:20-cv-03845-EMC, Document 61, dated Nov. 16, 2020 (18 pages).
*Google LLC* v. *Sonos, Inc.*, Sono, Inc.'s Patent L.R. 3-3 Invalidity Contentions, United States District Court, Northern District of California, San Francisco Division, Case No. 3:20-cv-03845, dated Dec. 14, 2020 (100 pages).
Notice of Allowance U.S. Appl. No. 16/186,168 dated Dec. 24, 2020 (12 pages).
Notice of Allowance for U.S. Appl. No. 16/186,211 dated Jan. 27, 2021 (5 pages).
"Whiteboard", MicrosoftWindows Technologies: Windows NetMeeting, Microsoft Corporation, Jun. 2, 1999, retrieved Dec. 11, 2020 from URL: https://web.archive.Org/web/19991013123712/http:/microsoft.com/windows/NetMeeting/Features/White board/default.ASP (1 page).
Brainfuse Tour, Brainfuse: Ignite Your Mind, retrieved Dec. 11, 2020 from URL: https://web.archive.org/web/20030831115823/http:/www.brainfuse.com/tour/slideshow_ . . . (1 page).
Doering et al., "Oracle Web Conferencing Administrator's Guide", Release 2 (2.0.4), Oracle Corporation, Jun. 2003 (168 pages).
Mutton, Paul, "NetDraw: A remote collaboration tool", jibble.org, 2003, retrieved Dec. 11, 2020 from URL: https://web.archive.org/web/20031203225815/http:/www.jibble.org/netdraw.php (4 pages).
Mutton, Paul, "NetDraw: A remote collaboration tool", jibble.org, 2013, retrieved Dec. 11, 2020 from URL: www.jibble.org/netdraw.php (4 pages).
Notice of Allowance for U.S. Appl. No. 16/186,168 dated Mar. 31, 2021 (5 pages).
Notice of Allowance for U.S. Appl. No. 16/186,211 dated Apr. 7, 2021 (5 pages).
Sonos Ex. 1002—File History, *Sonos* v. *Google*, 2021, IPR2021-00962 (613 pages).
Sonos Ex. 1003—Declaration of Douglas C. Schmidt, Ph.D., May 18, 2021, *Sonos* v. *Google*, IPR2021-00962 (220 pages).
Sonos Ex. 1007—Case Management and Pretrial Order for Claims Construction, *Sonos* v. *Google*, Oct. 15, 2020, IPR2021-00962 (2 pages).
Sonos Ex. 1009—Docket Navigator, Time to Milestones Search, Time to Trial Statistics, 2021, *Sonos* v. *Google*, IPR2021-00962 (2 pages).
Sonos Ex. 1009—Google's Preliminary Claim Constructions and Evidence Pursuant To Patent Local Rule 4-2, Jan. 11, 2021, *Sonos* v. *Google*, IPR2021-00962 (11 pages).
Sonos Ex. 1010—Excerpt from McGraw-Hill Dictionary of Scientific and Technical Terms, Sixth Edition, 2003, *Sonos* v. *Google*, IPR2021-00962 (3 pages).
Sonos Ex. 1011—Excerpt from Wiley Electrical and Electronics Engineering Dictionary, 2004, *Sonos* v. *Google*, IPR2021-00962 (4 pages).
Sonos Ex. 1012—Excerpt from The New Penguin Dictionary of Computing by Dick Fountain, 2001, *Sonos* v. *Google*, IPR2021-00962 (3 pages).

(56) References Cited

OTHER PUBLICATIONS

Sonos Ex. 1013—Excerpt from Newton's Telecom Dictionary, Mar. 2004, *Sonos v. Google*, IPR2021-00962 (4 pages).
Sonos Ex. 1014—Excerpt from Random House Webster's Computers Internet Dictionary by Philip E. Margolis, Third Edition, Jan. 2000, *Sonos v. Google*, IPR2021-00962 (3 pages).
Sonos Ex. 1102—File History, *Sonos v. Google*, 2021, IPR2021-00963 (613 pages).
Sonos Ex. 1103—Declaration of Douglas C. Schmidt, Ph.D., May 18, 2021, *Sonos v. Google*, IPR2021-00963 (235 pages).
Sonos Ex. 1107—Case Management and Pretrial Order for Claims Construction, *Sonos v. Google*, IPR2021-00963, Oct. 15, 2020 (2 pages).
Sonos Ex. 1108—Docket Navigator, Time to Milestones Search, Time to Trial Statistics, 2021, *Sonos v. Google*, IPR2021-00963 (2 pages).
Sonos Ex. 1109—Google's Preliminary Claim Constructions and Evidence Pursuant To Patent Local Rule 4-2, Jan. 11, 2021, *Sonos v. Google*, IPR2021-00963 (11 pages).
Sonos Ex. 1110—Excerpt from McGRAW-HILL Dictionary of Scientific and Technical Terms, Sixth Edition, 2003, *Sonos v. Google*, IPR2021-00963 (3 pages).
Sonos Ex. 1111—Excerpt from Wiley Electrical and Electronics Engineering Dictionary, 2004, *Sonos v. Google*, IPR2021-00963 (4 pages).
Sonos Ex. 1112 - Excerpt from The New Penguin Dictionary of Computing by Dick Fountain, 2001, *Sonos v. Google*, IPR2021-00963 (3 pages).
Sonos Ex. 1113—Excerpt from Newton's Telecom Dictionary, Mar. 2004, *Sonos v. Google*, IPR2021-00963 (4 pages).
Sonos Ex. 1114—Excerpt from Random House Webster's Computers Internet Dictionary by Philip E. Margolis, Third Edition, 1999, *Sonos v. Google*, IPR2021-00963 (3 pages).

*Sonos v. Google*—Petitioner's Power of Attorney, IPR2021-00962, May 20, 2021 (3 pages).
*Sonos v. Google*—Petitioner's Power of Attorney, IPR2021-00963, May 20, 2021 (3 pages).
*Sonos v. Google*—Sonos, Inc.'s Explanation of Multiple Petitions Challenging U.S. Pat. No. 10,140,375 and Ranking of Petitions, May 20, 2021, IPR2021-00962 (6 pages).
*Sonos v. Google*—Sonos, Inc.'s Explanation of Multiple Petitions Challenging U.S. Pat. No. 10,140,375 and Ranking of Petitions, May 20, 2021, IPR2021-00963 (6 pages).
*Sonos v. Google*—Sonos, Inc.'s Petition for Inter Partes Review of U.S. Pat. No. 10,140,375, Certificate of Service, May 20, 2021, IPR2021-00962 (2 pages).
*Sonos v. Google*—Sonos, Inc.'s Petition for Inter Partes Review of U.S. Pat. No. 10,140,375, Certificate of Service, May 20, 2021, IPR2021-00963 (2 pages).
*Sonos v. Google*—- Transcript of the Proceedings, 20-cv-03845-EMC, May 12, 2021 (29 pages).
*Sonos v. Google*, Sonos, Inc.'s Petition for Inter Partes Review of U.S. Pat. No. 10,140,375, May 20, 2021, IPR2021-00962 (73 pages).
*Sonos v. Google*, Sonos, Inc.'s Petition for Inter Partes Review of U.S. Pat. No. 10,140,375, May 20, 2021, IPR2021-00963 (68 pages).
Notice of Allowance for U.S. Appl. No. 16/186,168 dated Jun. 28, 2021 (5 pages).
Notice of Allowance for U.S. Appl. No. 16/186,211 dated Jun. 23, 2021 (5 pages).
Google v. Sonos; "Claim Construction Order;" United States District Court, Northern District of California, Case No. 20-vv-03845-EMC; 28 pages; dated Jun. 7, 2021.

* cited by examiner

PERSONALIZED NETWORK SEARCHING

CROSS-REFERENCE TO RELATED APPLICATIONS

This application is a continuation of U.S. patent application Ser. No. 15/854,208, filed Dec. 26, 2017 now U.S. Pat. No. 10,140,375, which is a continuation of U.S. patent application Ser. No. 15/492,513, filed Apr. 20, 2017now U.S. Pat. No. 10,398,898, which is a continuation of U.S. patent application Ser. No. 14/516,019, filed Oct. 16, 2014, now U.S. Pat. No. 9,679,067 which is a continuation of U.S. patent application Ser. No. 14/074,872, filed Nov. 8, 2013, now U.S. Pat. No. 8,886,626, which is a continuation of U.S. patent application Ser. No. 13/442,386, filed Apr. 9, 2012, now U.S. Pat. No. 8,612,415, which is a continuation of U.S. patent application Ser. No. 13/172,961, filed Jun. 30, 2011, now U.S. Pat. No. 8,166,017, which is a continuation of U.S. patent application Ser. No. 12/099,583, filed Apr. 8, 2008, now U.S. Pat. No. 8,015,170, which is a continuation of U.S. patent application Ser. No. 10/726,410, filed Dec. 3, 2003, now U.S. Pat. No. 7,523,096, all of which are incorporated herein by reference in their entirety.

FIELD OF THE INVENTION

The present invention relates generally to methods and systems for network searching. The present invention relates particularly to methods and systems for personalized network searching.

BACKGROUND

In general, most page visits on the World Wide Web are revisits; in other words, the user is returning to a web page previously visited. As search engines have improved, many users have turned to search engines for navigating to often-visited sites, rather than typing in uniform resource locators (URLs) or using browser bookmarks. A search engine performs the search based on a conventional search method. For example, one known method, described in an article entitled "The Anatomy of a Large-Scale Hypertextual Search Engine," by Sergey Brin and Lawrence Page, assigns a degree of importance to a document, such as a web page, based on the link structure of the web page. As these navigational queries become increasingly common, users are able to learn which queries will take them to their favorite sites. Bookmarks, however, can provide a benefit to the user. For example, a common use of bookmarks is for navigation to sites that search engines (such as the Google™ Search Engine) do not rank highly or that are otherwise hard to find via a search query.

Accordingly, bookmarks that the user continues to use are a valuable resource for the user. An Internet user often has difficulty propagating bookmarks between the various machines on which the user depends. For example, many users have a computer at work and at home. Often, the bookmarks relied on in the work setting are useful at home as well. In most cases, however, the user must manually synchronize the bookmark lists of the two machines. In addition, conventional methods of organizing bookmarks tend to be limited at best, making it difficult for the user to find a favorite site.

Some users have attempted to solve the propagation problem by using a commercial product that allows the user to store bookmarks on a server on the web, such as BlinkPro (Blink.com, Inc.; www.blinkpro.com) or BookmarkTracker (BookmarkTracker.com, Inc.; www.bookmarktracker.com). Such products allow the bookmarks to be managed and utilized from a browser application. In some cases, the user can also automatically synchronize each of the user's computers to the common list stored on-line. While storing the bookmarks on-line addresses the propagation problem, such systems fail td address the organizational problems inherent in conventional bookmarks.

Various other conventional bookmark-related software products provide the user with functionality to facilitate the use of bookmarks. For example, systems and methods for automatically organizing bookmarks on a client machine, searching previously-stored bookmarks by keyword, and integrating the back, history, and bookmark functions to improve the user's ability to visit previously visited sites have been described (see, e.g., *Integrating Back, History and Bookmarks in Web Browsers*, Kaasten, S. and Greenberg, S. (2001), In Extended Abstracts of the ACM Conference of Human Factors in Computing Systems (CHI'01), 379-380, ACM Press.). These tools, however, do not effectively leverage the user's preferences to provide personalized search results.

Thus, a need exists to provide an improved system and method for providing personalized network searching.

SUMMARY

Embodiments of the present invention provide systems and methods for personalized network searching. In one embodiment, a search engine implements a method comprising receiving a search query, determining a personalized result by searching a personalized search object using the search query, determining a general result by searching a general search object using the search query, and providing a search result for the search query based at least in part on the personalized result and the general result. An embodiment of the present invention may utilize ratings, annotations, history of use, or other data associated with the previously-identified uniform resource locator to locate and sort results.

Further details and advantages of embodiments of the present invention are set forth below.

BRIEF DESCRIPTION OF THE FIGURES

These and other features, aspects, and advantages of the present invention are better understood when the following Detailed Description is read with reference to the accompanying drawings, wherein.

DETAILED DESCRIPTION

Embodiments of the present invention comprise methods and systems for personalized network searching. In one embodiment, a search engine combines search results obtained from a global index or global indexes with those retrieved from a list of a user's favorite sites to produce a combined search result set. The combined result set may be sorted, marked, or otherwise used based on the user's preferences. Such an embodiment may provide the user with a mechanism to perform searches and visit favorite sites from one interface.

Figure 1:
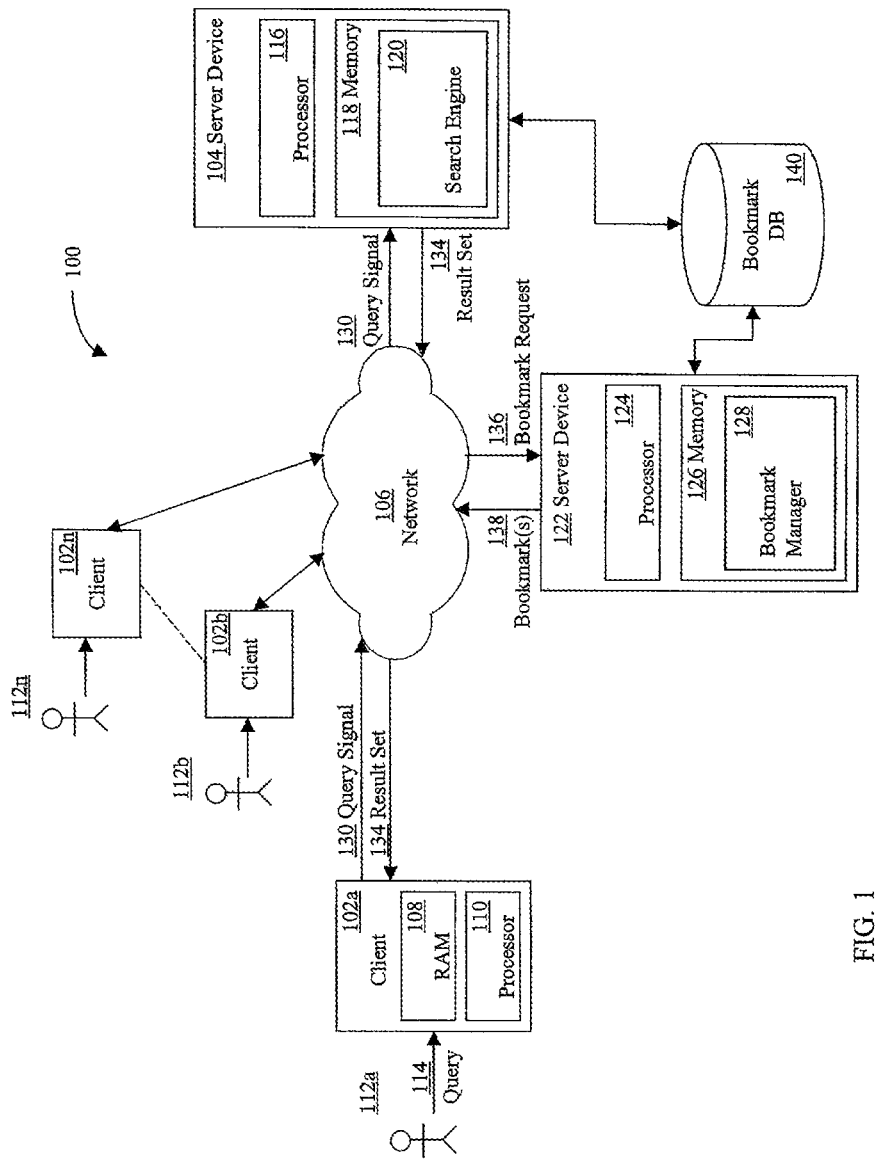
FIG. 1 is a block diagram illustrating an exemplary environment in which one embodiment of the present invention may operate.

Referring now to the drawings in which like numerals indicate like elements throughout the several figures, FIG. 1 is a block diagram illustrating an exemplary environment for implementation of an embodiment of the present invention. The system 100 shown in FIG. 1 includes multiple client devices 102a-n in communication with a server device 104 over a network 106. The network 106 shown includes the Internet. In other embodiments, other networks, such as an intranet may be used. Moreover, methods according to the present invention may operate within a single computer.

The client devices 102a-n shown each includes a computer-readable medium, such as a random access memory (RAM) 108 coupled to a processor 110. The processor 110 executes computer-executable program instructions stored in memory 108. Such processors may include a microprocessor, an ASIC, and state machines.

Such processors include, or may be in communication with, media, for example computer-readable media, which stores instructions that, when executed by the processor, cause the processor to perform the steps described herein. Embodiments of computer-readable media include, but are not limited to, an electronic, optical, magnetic, or other storage or transmission device capable of providing a processor, such as the processor 110 of client 102a, with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript.

Client devices 102a-n may also include a number of external or internal devices such as a mouse, a CD-ROM, DVD, a keyboard, a display, or other input or output devices. Examples of client devices 102a-n are personal computers, digital assistants, personal digital assistants, cellular phones, mobile phones, smart phones, pagers, digital tablets, laptop computers, Internet appliances, and other processor-based devices. In general, a client device 102a may be any type of processor-based platform that is connected to a network 106 and that interacts with one or more application programs. Client devices 102a-n may operate on any operating system capable of supporting a browser or browser-enabled application, such as Microsoft® Windows® or Linux. The client devices 102a-n shown include, for example, personal computers executing a browser application program such as Microsoft Corporation's Internet Explorer™, Netscape Communication Corporation's Netscape Navigator™, and Apple Computer, Inc.'s Safari™.

Through the client devices 102a-n, users 112a-n can communicate over the network 106 with each other and with other systems and devices coupled to the network 106. As shown in FIG. 1, a server device 104 is also coupled to the network 106. In the embodiment shown, a user 112a-n generates a search query 114 at a client device 102a. The client device 102a transmits the query 114 the server device 104 via the network 106. For example, a user 112a types a textual search query into a query field of a web page of a search engine interface or other client-side software displayed on the client device 102a, which is then transmitted via the network 106 to the server device 104. In the embodiment shown, a user 112a inputs a search query 114 at a client device 102a, which transmits an associated search query signal 130 reflecting the search query 114 to the server device 104. The search query 114 may be transmitted directly to the server device 104 as shown. In another embodiment, the query signal 130 may instead be sent to a proxy server (not shown), which then transmits the query signal 130 to server device 104. Other configurations are possible.

The server device 104 shown includes a server executing a search engine application program, such as the Google™ search engine. Similar to the client devices 102a-n, the server device 104 shown includes a processor 116 coupled to a computer-readable memory 118. Server device 104, depicted as a single computer system, may be implemented as a network of computer processors. Examples of a server device 104 are servers, mainframe computers, networked computers, a processor-based device, and similar types of systems and devices. Client processor 110 and the server processor 116 can be any of a number of computer processors, such as processors from Intel Corporation of Santa Clara, Calif. and Motorola Corporation of Schaumburg, Ill.

Memory 118 contains the search engine application program, also known as a search engine 120. The search engine 120 locates relevant information in response to a search query 114 from a user 112a-n.

In the embodiment shown, the server device 104, or related device, has previously performed a crawl of the network 106 to locate articles, such as web pages, stored at other devices or systems connected to the network 106, and indexed the articles in memory 118 or on another data storage device. Articles include, for example, web pages of various formats, such as HTML, XML, XHTML, Portable Document Format (PDF) files, and word processor, database, and application program document files, audio, video, or any other documents or information of any type whatsoever made available on a network (such as the Internet), a personal computer, or other computing or storage means. The embodiments described herein are described generally in relation to HTML files or documents, but embodiments may operate on any type of article, including any type of image.

In an embodiment of the present invention, the search engine 120 also searches a user's list of favorite sites, which personalizes the search. For example, a user's list of favorite sites may be saved as a list of bookmarks. Bookmarks are objects that include a uniform resource locator (URL) identified by a user. A bookmark may be referred to by different terms in different applications. For example, Microsoft® products often refer to bookmarks as "favorites." Similar to the client devices 102a-n and the server device 104, the server device 122 shown includes a processor 124 coupled to a computer-readable memory 126. As with server device 104, server device 122, depicted as a single computer system, may be implemented as a network of computer processors or may be incorporated into the server device 104. Examples of a server device 122 are servers, mainframe computers, networked computers, a processor-based device, and similar types of systems and devices.

Memory 126 contains the bookmark manager application program, also known as a bookmark manager 128. In the embodiment shown, the bookmark manager 128 is a C++ program, however, the bookmark manager 128 may be constructed from various other programming languages as well.

Referring still to the embodiment shown in FIG. 1, the bookmark manager 128 comprises an interface so that a user 112*a* may manage bookmarks on the server. For example, in one embodiment, the bookmark manager 128 provides a browser-based application that allows the user to create, modify, delete, and save bookmarks on the network. The application may comprise, for example, HTML and JavaScript, an ActiveX component, or a Java applet. The bookmarks are saved in the bookmark database 140. In an embodiment of the present invention, the bookmark manager 128 also provides the data stored in the bookmark database 140 to the search engine 120.

When the search engine 120 performs a search in response to the query search query signal 130, the search engine 120 searches previously indexed articles. The search engine 120 also creates a bookmark request 136, corresponding to user 112*a*. The bookmark manager 128 responds by sending one or more bookmarks 138 to the search engine 120. The search engine 120 utilizes the bookmarks, 138 to search sites previously identified by the user 112*a*. The search engine then merges the results of the two searches to provide a result set 134 to the client 102*a*.

It should be noted that the present invention may comprise systems having different architecture than that which is shown in FIG. 1. For example, in some systems according to the present invention, server device 104 and server device 122 may comprise a single physical or logical server. The system 100 shown in FIG. 1 is merely exemplary, and is used to explain the exemplary methods shown in FIGS. 2 through 4.

In embodiments of the present invention, a user 112*a* can track their conventional browser bookmarks using server-side storage. These bookmarks can then be made available to the user on all the various computers the user uses and can be integrated with browser bookmarks and with the browser (e.g., via a toolbar). For example, a user's set of bookmarks can be primed on a server by having the user POST their bookmarks file to the server, and the user can be permitted to download the bookmarks as a bookmarks file or other related representation. Alternatively, client-side software may implicitly manage the server-side storage. In one embodiment, the bookmarks may comprise a continuous user rating, e.g., 0.0-1.0, rather than just a discrete bookmarked-or-not bit. In another embodiment, a user can integrate per-page annotations into their data regarding bookmarks or favorites. In yet another embodiment, a user can store multiple user personalities (e.g., previously defined sets of bookmarks) and can receive recommendations based on the set of bookmarks saved by users with similar tastes as derived by their bookmarks or other stored or monitored preferences.

Various methods may be implemented in the environment shown in FIG. 1 and other environments according to the present invention. For example in one embodiment, a user 112*a* enters a search query 114, which a client 102*a* transmits as a query signal 130 to a server device 104 over a network 106. The server device 104 executes a search engine 120. The search engine 120 receives the query signal 130. The search engine 120 determines a personalized result by searching a personalized search object using the search query.

Examples of a personalized search object include, for example, a list of bookmarks or favorites and the history list of a browser. The search engine 120 also determines a general search result by searching a general search object. The general search object may comprise, for example, an index of articles, such as, for example, those associated with a conventional search engine. The search engine 120 provides a search result to the user based at least in part on the personalized result and the general result. In another embodiment, the search engine 120 provides a search result to the user based solely on the personalized result.

The search engine 120 may generate the search result by combining the general results and the personalized results. The search engine may instead provide separate lists: one containing the general search result and a second containing the personalized search result. The search engine 120 transmits the search result as a result set 134 to the client 102*a*.

In one embodiment, the search engine 120 returns the list sorted as in a conventional search engine and with the personalized search results indicated in some way, such as, for example, highlighted or shown with a symbol beside the personalized search result. In another embodiment, the search engine sorts the combined results list based at least in part on a rating that the user 112*a* has associated with the uniform resource locator.

The results may be sorted in a number of ways. For example, in one embodiment, the combined results list is sorted based at least in part on an annotation or rating that has been associated with the user 112*a* and the uniform resource locator. The results may instead or further be sorted based on whether the result in the combined result list originated in the global results list or in the personalized search result. For example, the user 112*a* may wish to see their personalized results displayed at the top. The results may be instead or further sorted based on a rating of a page provided by or created for the user 112*a*. In one embodiment, rather than changing the sorting order of the pages provided in a result set, the search engine 120 marks results that originated in the user's personalized search results. A fuzzy algorithm may also be employed to sort the results. For example, the sorting of the combined results list may only slightly favor the personalized search result. In another embodiment, the results list is sorted by measures indicating user preferences. For example, if many of the user's bookmarks are computer-related, computer-related results are sorted closer to the top of the result set 134 than non-computer related results. Other operations may also be performed on the results based at least in part on user-specific information. For example, the results may be interleaved, merged where necessary or desired, presented with annotations, or presented in other ways that provide useful information to the user 112*a*.

An embodiment of the present invention may comprise features to facilitate community building. For example, in one embodiment, the uniform resource locator comprises a community bookmark. The bookmark may be shared by a set of users or may be transmitted by one user and received by another. The second user can then perform personalized queries that are based, at least in part, on the shared bookmark. In another embodiment, a cluster of users is identified based at least in part on the bookmarks and annotations that they have previously identified.

A user 112*a* may specify bookmarks explicitly. In one embodiment, the bookmarks are implicitly identified based on a measure of the behavior of the user. For example, in one embodiment, the implicit measure comprises the linger time. In other words, if a user spends a great deal of time on a site, it is identified as a bookmark for later personalized searches. In other embodiments, the implicit measure may comprise at least one of the quantity of repeat visits to the site or the quantity of click-throughs on the site. In one embodiment, temporal decay of ratings may be utilized so that unused or rarely used bookmarks, whether explicitly marked or implicitly marked, become unmarked over time. Other implicit measures include printing the page, saving the page, and the amount of scrolling performed on the page.

In one embodiment of the present invention, the user associates a text string with a uniform resource locator (URL). The text string may comprise, for example, a search query, a URL-format text string, or a short-hand indicator of the URL. The client 102*a* receives the personalized association data associating the text string with the URL and stores the personalized association data in a personalized search object. The client 102*a* subsequently receives an input signal comprising the search string, determines the URL associated with the text string and displays an article associated with the URL. The article may be received from a global network element, such as a web server.

Figure 2:
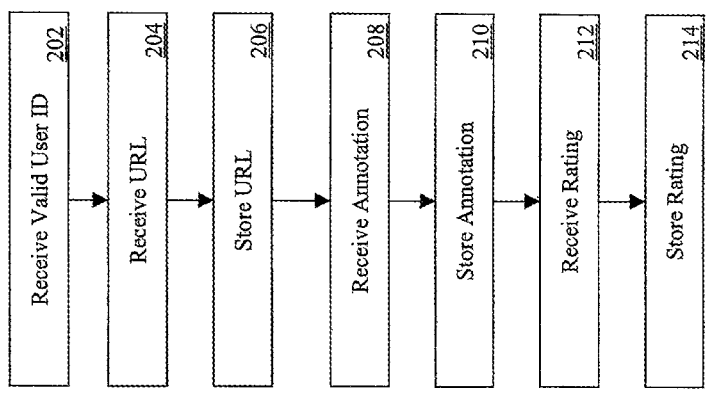
FIG. 2 is a flowchart, illustrating a method for storing bookmarks, ratings, and annotations in an embodiment of the present invention.

FIG. 2 is a flowchart illustrating a method for storing bookmarks, ratings, and annotations in an embodiment of the present invention. In the embodiment shown, a user 112*a* navigates to a site by typing in a URL or other means. The user 112*a* determines that the site is useful and that the user 112*a* will revisit the site. Accordingly, the user 112*a* bookmarks the site using a bookmark manager 128. The user 112*a* may access the bookmark manager 128 in various ways. For example, in one embodiment, the user 112*a* accesses a client-side application via a built-in user-interface element or one available via a toolbar or other available plug-in in a browser executing on the client 102*a*. The button causes a popup window to be displayed in which the user enters an annotation and rating. When the user clicks a submit button, the information is submitted to the bookmark manager 128 for storage as a bookmark in the bookmark database 140.

In the embodiment shown, the bookmark manager 128 first receives a valid user identifier (ID) 202 from the client 102*a*. Users who desire synchronization across different browsers/computers or other types of personalization need to identify themselves to the bookmark manager 128 to some extent so that the bookmark manager 128 has a primary key with which to store a user's bookmarks. The bookmark manager 128 can perform the identification and authentication in numerous ways. For example, in one embodiment, the IP address is tracked throughout a session. In another embodiment, the authentication is done via a user manager system. In another embodiment, a cookie on the client 102*a* may include user-identifying information, which is supplied to the bookmark manager 128 by the client 102*a*.

The bookmark manager 128 then receives the URL for the site that the user identifies 204. The bookmark manager 128 stores the URL, its rating(s), and its annotations) in the bookmark database 140 for later retrieval 206. It is likely that a user already has a set of bookmarks (or several sets of bookmarks) that they would like to make available for their searches. Accordingly, in one embodiment, the bookmark manager 128 includes a mechanism for migrating that data to the bookmark database 140. The hierarchy of bookmarks can be used as implicit annotations on the named URLs and can at least be preserved when synchronizing the bookmarks among browsers. In another embodiment, the full text of an article when it was last visited serves as an annotation of the URL. In still another embodiment, as bookmarks are edited on a supported browser's native interface, the corresponding edits are made to the server-side bookmarks.

In one embodiment, the bookmark manager 128 provides a server-side management tool via an HTML interface (which, again may mirror changes into a supported browser's native bookmarks). Synchronization of client and server-side bookmarks may increase adoption of the bookmark manager 128 if the user can at least manually synchronize server-side bookmarks into client-side browser bookmark lists. In one embodiment, the management tool also displays the bookmark rating for a given page and allows the user 112*a* to manipulate the rating and/or an annotation associated with the page. In another embodiment, bookmark manager 128 supports listing recently rated pages to facilitate returning to recently bookmarked pages, thus enabling a work-list like review of a surfing session.

Referring still to FIG. 2, the bookmark manager 128 also receives 208 and stores 210 an annotation of the URL in the bookmark database 140. The annotation is a remark that the user provides regarding the URL. The annotation may simply be a text string stored in a database 140 and associated with the URL. The annotation may be instead stored in a standardized format, see, e.g., *Annotea: An Open RDF Infrastructure for Shared Web Annotations*, J. Kahan, M. Koivunen, E. Prud'Hommeaux, and R. Swick (2001), In Proceedings of WWW10, May 1-5, 2001 Hong Kong.

In the embodiment shown, the bookmark manager 128 also receives 212 and stores 214 the rating of the site provided by the user 112*a* in the bookmark database 140. For example, in one embodiment, the user 112*a* clicks a rating button. In response, the user 112*a* is presented with a series of ten radio buttons labeled 0.0 through 1.0. The user selects one of the radio buttons and clicks submit. The bookmark manager 128 receives the rating and the URL and saves the two data values in the bookmark database 140. FIG. 2 is merely exemplary. In other embodiments the user may provide more or less information related to a site to the bookmark manager 128.

Although in the embodiment shown, the reception and storage of the URL, annotation, and rating are shown as linear steps, they may be performed in other ways as well. For example, the bookmark manager may receive the URL, annotation, and rating together and perform one step to store them in the bookmark database 140.

The data stored in the bookmark database 140 may be updated fairly frequently as pages are bookmarked (or the bookmark is toggled, or a rating slider is changed).

Figure 3:
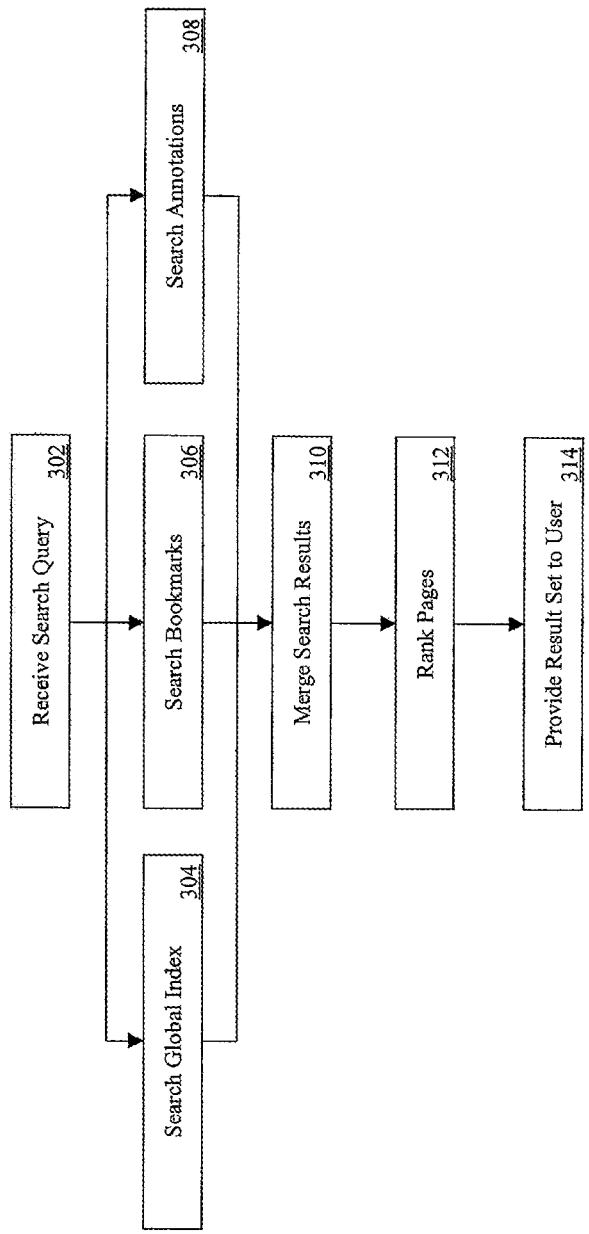
FIG. 3 is a flowchart illustrating a method of performing a network search in one embodiment of the present invention.

FIG. 3 is a flowchart illustrating a method of performing a network search in one embodiment of the present invention. Embodiments of the present invention may combine conventional network searches with, for example, personalized searches utilizing information provided by the user previously or in conjunction with the submission of the search. In the embodiment shown in FIG. 3, the search engine 120 receives a query signal 130 from a client (102*a*) 302. The search engine 120 responds to the query signal 130 by performing a search. In the embodiment shown, the search comprises three sub-processes, which may be run in parallel. These three processes comprise: searching global indices 304, searching the URLs stored as bookmarks 306, and searching annotations 308. Other embodiments may employ a fewer or greater number of sub-processes: For example, in one embodiment, the URLs present in the navigation history of the browser are searched.

Conventional search engines search global search objects, such as global search indices. Embodiments of the present invention are also capable of searching personal search objects, such as bookmarks, annotations, ratings, and other objects. In one embodiment, such searching comprises reading a list of URLs from the bookmark database 140, and for each page, searching the various parts of the page using the search query 114 submitted by the user 112a. In another embodiment, an agent operating on the client 102a searches a personal search object stored on the client 102a or in a repository accessible to the client 102a via the network 106.

Searching annotations comprises searching the user-entered annotations using the search query 114 submitted by the user 112a. For example, a user 112a may enter the term "boat" as an annotation for a page comprising marine supplies. If the users 112a enters "boat" as part of the search query 114 utilized by the search engine 120, the page with the "boat" annotation will be returned by the search annotations component. Another embodiment of the present invention searches not only the pages that the user has bookmarked or annotated, but also pages similar to the pages that the user has bookmarked or pages with similar annotations.

Each of the sub-processes 304, 306, and 308 shown may generate a separate result set in the embodiment shown. In other embodiments, the sub-processes 304, 306, and 308 may be combined and/or configured to provide a combined result set automatically. The result sets may overlap to some degree. In the embodiment shown, the search engine 120 merges the search results into one list 310. The search engine 120 then ranks the pages 312. Various methods may be utilized to rank the pages. For example, the search engine 120 may rank results returned via annotation based on their user-based ratings, if any, then per the standard ranking algorithm. Several examples are set out below. The search engine 120 then provides a sorted result set 134 to the user 112a requesting the search 314.

In another embodiment, the user supplies an annotation that is associated with a URL. The annotation is stored on a per-user basis to supplement the search results and to further improve scoring. Other users who share similar interests with the user who provided the annotation may use the annotation.

Embodiments of the present invention may make further use of the annotation. For example, in one embodiment, the search engine 120 searches for the keywords provided in a search query 114 in user-supplied annotations, e.g., treating those annotations as user-specific anchor text that refer to the annotated URL. The result set generated by a search engine in one such embodiment reflects the union of the global index and the results from the annotation keyword search.

Embodiments may also utilize other data, such as user ratings to determine the ranking of the results, to mark the results, or for other purposes. For example, in one embodiment, the page rankings that the search engine 120 provides are not affected by the user-supplied ratings for each page, but an indicator, such as an asterisk or other small image, identifies specific results that are rated based on ratings data stored in the bookmark database 140.

Embodiments of the present invention may combine the results of several types of results, or may present the results separately. For example, in one embodiment, a user 112a submits a search query 114. The search engine 120 searches a global search object and presents the results in one list. The search engine 120 also searches a personal search object and presents the results of the search in a second list.

In another embodiment of the present invention, the search engine 120 also uses a user-applied rating to rank the pages. For example, a user 112a applies a rating (e.g., between 0.0 and 10.0) to each of the bookmarks stored in the bookmark database 140. The search engine 120 utilizes the user-applied rating in determining where in the result set 134 a particular article should be displayed. For, example, a rating of 0.5 might represent indifference, and lower ratings would penalize a result while higher ratings would make it score higher. In yet another embodiment, the search engine 120 more highly scores unrated pages that are similar to the content of highly rated URLs. In one embodiment, in which a large set of diverse user ratings and annotations have been stored, the search engine 120 may provide additional related features such as page suggestions based on similar users' ratings, e.g., via simple clustering approaches.

The term or alternate URL associated with the primary URL is a distinct token in the personalized search that indicates a desire of the user not to search for the term or navigate to the alternate URL, as would be the case in a conventional browser application, but instead to immediately go directly to a specific page that is associated with the term or alternate URL for the user 112a.

In one embodiment, a user 112a associates a specific term or alternate URL with a primary URL, such as the URL associated with a previously-stored bookmark in the bookmark database 140. For example, the user 112a may enter a term in one text box and a URL in another text box and then click a button to associate the two. The association is then stored in a computer-readable medium on the client machine 102a or in a computer-readable medium accessible by a server 104, such as in the bookmark database 140. The term or alternate URL becomes a "speed-dial" navigation link to the URL. In one embodiment, the user 112a enters the term in a query search box and clicks a link or control, such as a standard search link or button, and, rather than performing a search for the term using a search engine, the browser or browser-enabled application retrieves the URL previously associated with the term and immediately jumps to the site associated with the URL. In another embodiment, a keyboard binding causes the browser to jump to the site associated with the URL. In either case, the command by the user 112a causes a behavior to occur that is personalized to the user as opposed to the conventional query behavior common to all users of the search engine. In other words, no search is performed; the browser simply navigates to the URL associated with the term in lieu of performing the search.

In yet another embodiment, the user 112a enters the alternate URL in the address field of the browser and clicks the "go" control or otherwise causes the browser to evaluate the alternate URL. Rather than navigating to the URL, the browser first searches for the alternate URL in the list of URL's associated with bookmarks. If the alternate URL is found, the browser navigates directly to the primary URL that is associated with the alternate URL.

For example, in one embodiment, a user 112a associates the term "home" with the user's corporate intranet page. The user 112a enters the term "home" in a text box and the URL for the corporate intranet page in another text box and clicks a control to associate the two. Alternatively, the user clicks a control during display of the corporate intranet page that provides the user 112a with an opportunity to associate the term and the page. Subsequently, the user 112a enters the term "home" in a search field and clicks the search control. Since the term "home" has been associated with the corporate intranet homepage, the browser immediately navigates to the user's corporate intranet homepage rather than executing a search for the term "home." The user 112a may want to select terms or phrases for association that are unlikely to be used in standard searches. For example, the user 112a may use a single number (e.g., "1") to associate with a URL.

In another embodiment, the user 112a associates the alternate URL "www.myhome.com" with the actual or primary URL for the user's 112*a* personal homepage. When the user 112*a* enters the URL "www.myhome.com" in the address line of the browser executing on the client 102*a*, the browser locates the association between the alternate and primary URL's and navigates to the page identified by the primary URL, the user's personal home page.

An embodiment of the present invention may provide various user interfaces. For example, in one embodiment, two distinct user interfaces are provided: one for novice users and one for advanced users. The novice interface may simply give visual feedback about whether a page is bookmarked or not and permits the user to toggle that state with a simple click. The richer, advanced-user interface may utilize a slider control reflecting a rating for the current page and a personality-mode (e.g., work/home/hobby) drop-down box that switches among different rating sets. Another embodiment includes an intermediate-level interface that includes a bookmark (vote positive) and a booknegate (vote negative) button (not unlike the voting buttons as part of the advanced features of some search toolbars, such as the Google Toolbar).

A user interface according the present invention may also include a personalized result page that includes a visual indication of a result that was reordered due to personalization. In one embodiment of the present invention, the user interface includes a means for toggling the personalization of results. For example, in one embodiment, the user clicks a button on the HTML interface to turn on personalization. If personalization is active, the user may click a button disabling personalization. Such a feature addresses the need to depersonalize results before sharing a query result links with other users (e.g., via email).

One embodiment of the present invention supports applying bookmarks directly via a results page. For more advanced users, bookmark manager 128 may support a "Rank these results" link that lets advanced users select a rating (perhaps using radio buttons) for each result on a given page. Because of privacy concerns, bookmark manager 128 may disallow access to "View bookmarks" to not-logged-in users; nevertheless, search results may be appropriately personalized based on just the cookie of not-logged-in users.

Embodiments of the present invention implement various measures to help encourage user adoption. For example, although not. all users may be willing to expend the effort to provide ratings, an embodiment of the present invention provides noticeable benefits for relatively low effort on the part of the user. In addition, by incorporating bookmark synchronization, an embodiment of the present invention helps drive adoption.

Embodiments of the present invention may also implement network and community features to foster adoption of the service. For example, as described above, an embodiment of the present invention may utilize like-user recommendations to locate and rank results. One embodiment of the present invention implements user groups and friendlists whereby a user can choose to expose a bookmark list to friends or the public at large. In another embodiment, a user has the ability to transparently overlay a weighted set of bookmarks onto their own set of bookmarks.

An organization implementing an embodiment of the present invention may utilize partnerships to encourage adoption of the service. For example, a service provider may encourage partner sites to display a "bookmark this page!" snippet on their homepages and other content pages. For the partner, an embodiment of the present invention provides a means to ask users to opt-in to making it especially easy to get at their site via a search. And for users it's a nice reminder to mark the page or add an annotation. For the provider of the bookmark and search service, such an arrangement helps introduce users to the idea of bookmarks at the moment it matters most: when they are visiting a page they are interested in. It may be advantageous to (e.g., for security reasons) to have partners wishing to display a "bookmark this page!" link to register with the service provider first. Registration with the service provider also helps the service provider to develop relationships with additional content providers.

A provider of a bookmark service may receive various benefits from implementing the service. For example, the provider is able to collect data concerning users' attribution of value on pages.

One embodiment of the present invention utilizes an anti-spamming mechanism to avoid the problem of companies with a financial interest in driving traffic to their sites attempting to falsify end user interest in their pages. In one embodiment, the search engine 120 addresses this problem by not trusting the bookmark signal globally, but leveraging it only for user personalization. In one embodiment, the bookmark manager employs credit card validation (for identification only) and/or CAPTCHAs (Completely Automated Public Turing Test to Tell Computers and Humans Apart) to gain evidence that bookmark manager 128 is interacting with a legitimate user.

An embodiment of the present invention may provide other features as well. For example, one embodiment provides collaborative link recommendations. When logged in, a user 112*a* is provided a link with anchor text, such as "See related bookmarks for users similar to you." The linked page provides other suggested links that may be of interest to the user 112*a*. This feature may be integrated into or separate from the main results page.

An embodiment of the present invention may provide useful information to the provider of the bookmark service. For example, for sites that users visit most frequently, client-side bookmarks are often the tools of choice. An unfortunate consequence is that those page visits are largely hidden from the provider of a search service. With bookmarks being used as a navigational tool according to the present invention, the service provider has access to the previously unavailable data and may be better equipped to provide user-personalized portals. For example, pattern recognition might let the service provider realize that a user visit various stock quotes every Monday morning, checks CNN.com in the afternoons, etc. In such an embodiment, the search engine 120 may anticipate the pages that users will likely require.

An embodiment of the present invention may also improve the relevance of advertisements presented in conjunction with search results. For example, one embodiment of the present invention is able to use bookmarks to cluster user interests and leverage click-through data of various advertisements for similar users to present even more relevant advertisements. In other words, the advertisements are based, at least in part, on the search results returned based on the bookmarks or other personal search object. This feature provides numerous benefits. Not only are users more likely to be satisfied because the advertising is more targeted, but the click-through rate for the service provider may increase, resulting in increased revenue.

In one embodiment, a user may share or overlay bookmarks. For example in one embodiment, a user is able to open up their bookmarks for others to view. In another embodiment, a user is able to aggregate other users' bookmarks into their own set of bookmarks (either via copying or via an overlaid reference semantics). Such a feature may prove useful for community building (e.g., "Add this group's bookmarks to your favorites" when joining a new mailing list). In one such embodiment, the bookmark indicators in results pages distinguish between those pages explicitly bookmarked by the user from those gathered by others. Given a canonical URL through which to reference another individual/organization's bookmarks, the service provider can derive a sense of the popularity of a person's links and weight those bookmarks correspondingly (a la PageRank applied to the subgraph of bookmark interlinks).

One embodiment of the present invention fosters community and relationship building. In one embodiment, the search engine is able to recognize clusters or pairs of users having similar interests. Such an embodiment is able to suggest other users with which to network.

An embodiment of the present invention may include various other features as well. For example, in one embodiment, linger time and/or repeat visits is used to implicitly bookmark a page. Other implicit measures, such as the ones described above, may also be utilized. With this feature, a toolbar slider may start inching to the right as you view a given page (and should attempt to alert the user that the change has occurred, perhaps by flashing). The user explicitly dragging the slider would override the setting (and turn off the implicit rating improvement for this visit to the site).

Figure 4:
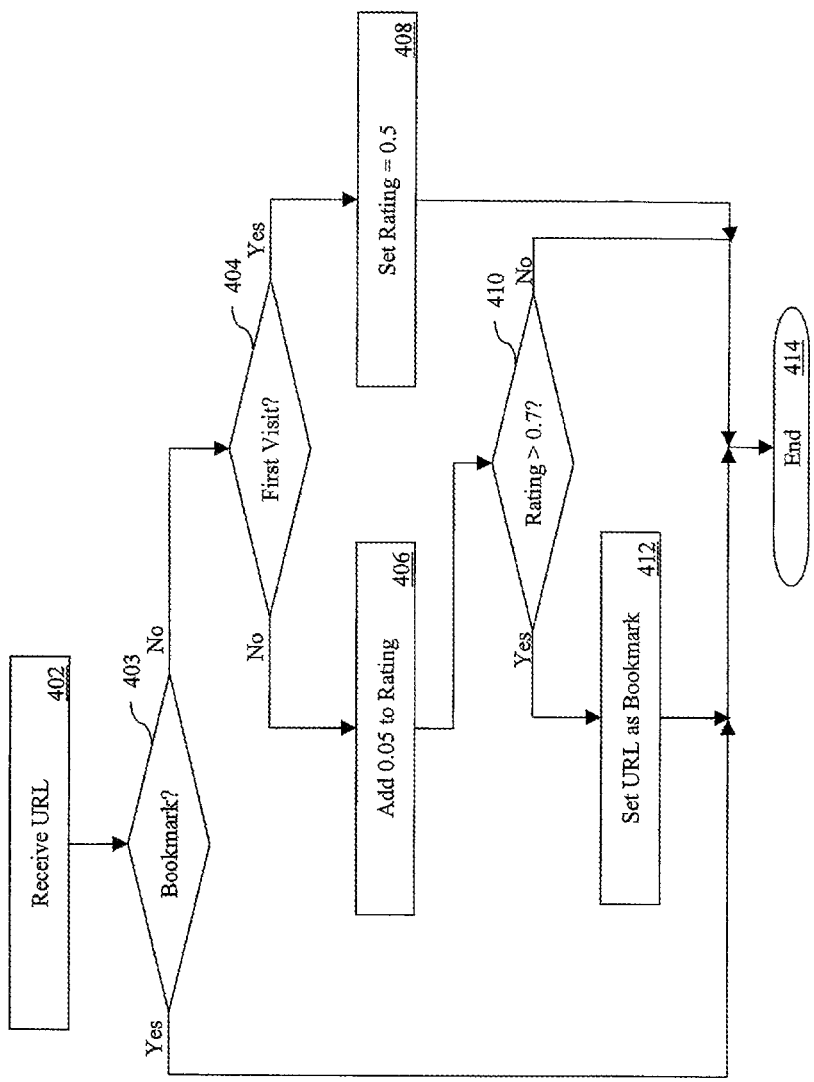
FIG. 4 is a flowchart illustrating a process of implicitly rating a page 'One embodiment of the present invention.

FIG. 4 is a flowchart illustrating a process of implicitly rating a page in one embodiment of the present invention. In the embodiment shown, the bookmark manager 128 receives a URL 402. The bookmark manager 128 determines whether or not the URL has been saved as a in the bookmark database 140 as a bookmark 403. If so, the process ends 414. Otherwise, the bookmark manager 128 determines whether this is a first visit by the user to the URL 404. If so, the bookmark manager adds the bookmark to the bookmark database 140 and sets the rating equal to 0.5 408. The process then ends 414. In the embodiment shown, the bookmark manager 120 does not identify the URL as a bookmark, but merely adds an entry to maintain the rating of the site.

If the bookmark has been visited before, the bookmark manager 128 adds 0.05 to the value of the rating 406. Once the rating has been set or adjusted, the bookmark manager 128 determines whether the rating is greater than or equal to 0.7 410. The value 0.7 is a threshold for implicitly creating a bookmark and may be adjusted in various embodiments. If the value is greater than or equal to 0.7, the bookmark manager 128 marks the URL as a favorite in the bookmark database (140) 412. The process then ends 414. If the value is less than 0.7, the process ends, and the bookmark is not added to the bookmark database 140. Another embodiment of the present invention utilizes linger time in addition to or instead of page visits for implicitly bookmarking pages.

An embodiment of the present invention may use the ratings, annotations, or any other data in presenting search results. In several of the examples described above, the data is used to sort or mark search results shown to a user 112a. In one embodiment, the data is used to exclude search results from those shown to the user.

Embodiments of a rating process according to the present invention may provide other features as well. For example, one embodiment provides the capability to search previously stored bookmarks as a completely separate search experience rather than integrating the results into the basic results page. In one such embodiment, the interface on the client 102a presents the user with two checkboxes. By checking the first checkbox, the user 112a specifies that the search engine 120 should search global indices. By checking the second checkbox, the user 112a specifies that the search engine 120 should search the user's bookmarks. The user 112a is able to vary the search based on the particular type of search that the user 112a wishes to perform. In another embodiment, hits due to indexed annotations are presented separately at the top, and hits due to results that were otherwise found are marked in their usual ranking position and may also be shown at the top. The links presented at the top of the result set 134 may not include snippets.

To mitigate privacy concerns, embodiments of the present invention may require users to opt-in to the tracking. In such an embodiment, the system alerts the user when personalized search is in effect and provides a simple mechanism for reverting to generic search. In such an embodiment, bookmark data may be stored in a secure data center separate from a user's other personal data.

Various interface designs may be implemented in an embodiment of the present invention. For example, in one embodiment, marking of pages of interest and non-interest is provided via JavaScript bookmarklets. One such embodiment displays the user-specified ranking (if any) by usurping the PageRank display to be user-specific. The color changes when the bookmark rating exceeds the mark threshold (0.7 in FIG. 3).

In another embodiment of a user interface according to the present invention, the user is provided with a simple user interface for adding an annotation for an arbitrary page, such as via a new menu option in the toolbar's Info drop-down or via a star button in the browser or a toolbar or a plug-in of the browser. The bookmarked or booknegated pages in results sets are displayed and the bookmarks and booknegates may be edited directly in the results list.

In the embodiment shown in FIG. 1, client 102a transmits query signal 130 to the server device 104 executing the search engine 120. In another embodiment, the server device 122 executing the bookmark manager 128 may receive queries directly. In one such embodiment, seven queries are defined to retrieve and/or save various pieces of data. In each of the queries, the user identifier is provided as a primary identifier.

In a first query, a user provides a rating of a page. The rating may be a simple yes/no or up/down rating or may include a rating across a scale. The response may just be the new bookmark rating (for example, as an ASCII-encoded integer). For a query implementing an up/down rating, the rating may be boosted or dropped slightly along a scale. An example of a rating query is:

GET/set-bookmark?rating=NUM&url-URL&annotation=ANNOTATION.

In a second query, information for new pages visited by the user is requested. Such a query may include a features parameter, which may be extended to explicitly ask for bookmark ratings. The response may be something like: "Rank_I:1:8." One example of such a query is:

GET/search?client=navclient-auto&q=info:URL.

In a third query, a bare bookmark rating is requested for a set of documents. In the query shown, the URLLIST is a list of URLS, separated by spaces, re-urlencoded, and DocIds is a space-separated list of docids, url-encoded. Results for all of these are returned, one per line. One example of such a query is:

GET/get-bookmarks?urls=URLLIST&docids=DOCIDLIST.

In a fourth query, an annotation for a URL is requested. In one embodiment, when the URL is not specified, the server returns a list of URLs that have bookmark annotations in a HTML user interface that permits a user to view and edit those annotations. One example of such a query is
GET/annotations?url=URL.

A fifth query transmits a list of bookmarks to a server. One example of a bookmark POST acceptor is as follows:
POST/set-bookmarks.

In the POST acceptor query, the POST-data may have a Content-Type of "text/html" and be a favorites list represented in HTML, for example, in the format Microsoft Internet Explorer™ exports.

A sixth query provides a means to get a full bookmark list in XML format. One such query is as follows:
GET/get-bookmarks.xml.

A seventh query provides a means for searching an annotation and returning URLs or Docids that match the query terms provided in the query. One such query is as follows:
GET/search-annotations?q=QUERYTERMS.

Embodiments of the present invention provide numerous advantages to the user and to the provider of the search service. An embodiment of the present invention improves the user experience by providing personalized search results and rankings.

An embodiment of the present invention provides advantages to the provider of a search service by (1) increasing the stickiness of the search experience by giving users a compelling reason to identify themselves and share their interest in topics with the provider, and (2) gathering better data regarding the relevancy of pages to different users and different classes of users.

In an embodiment of the present invention, the user providing bookmarks to the service provider enables the search provider to personalize the search for them. The feature can be viewed as a server-side generalization of bookmarks integrated with annotations. Users are able to share that personalization data across different browsers (e.g., work and home) if desired and hence eliminate the drudgery associated with managing bookmarks. An embodiment of the present invention also unifies all navigational queries under a single experience.

The foregoing description of the preferred embodiments of the invention has been presented only for the purpose of illustration and description and is not intended to be exhaustive or to limit the invention to the precise forms disclosed. Numerous modifications and adaptations thereof will be apparent to those skilled in the art without departing from the spirit and scope of the present invention.

What is claimed is:

1. A system, comprising:
a first device comprising one or more processors and memory, the first device comprising a first application program stored in the memory of the first device, the first application program to:
receive a modification to a set of objects; and
transmit an indication of the modification to the set of objects;
a second device comprising one or more processors and memory, the second device comprising a second application program stored in the memory of the second device, the second application program to:
receive the indication of the modification to the set of objects;
modify, responsive to the indication, the set of objects stored on the second device;
receive, via an input interface of the second device, a query;
present, through an output interface of the second device, in response to the query, a combined search results set generated via one or more search sub-processes, the combined search results set including at least two of:
an object from the set of objects modified via the first device;
an object from a first index; or
an object from a second index.

2. The system of claim 1, comprising:
the first device to transmit the indication of the modification to a server; and
the second device to receive the indication of the modification to the set of objects from the server.

3. The system of claim 1, comprising:
the first device to transmit the indication of the modification to a server; and
the server to synchronize the set of objects stored on the server based on the indication of the modification, and further synchronize the set of objects with a plurality of other devices associated with the first device, the plurality of other devices comprising the second device.

4. The system of claim 1, comprising:
the first device to modify, responsive to receipt of the modification via the first device, the set of objects stored in a device-side storage on the first device.

5. The system of claim 1, wherein the modification to the set of objects received by the first device comprises an indication to create an object to add to the set of objects, the system comprising:
the first device to add the object to the set of objects in a device-side storage of the first device, and add the object to the set of objects stored on a server.

6. The system of claim 1, wherein the set of objects comprises a set of bookmarks.

7. The system of claim 1, wherein the set of objects comprises a set of favorite items.

8. The system of claim 1, wherein the set of objects comprises an identifier to a resource.

9. The system of claim 1, wherein the set of objects comprises an identifier to an audio file.

10. The system of claim 1, wherein the set of objects comprises an identifier to an audio file that is accessible via the network.

11. The system of claim 1, wherein the first application comprises at least one of a manager, HTML-based application, JavaScript-based application, an ActiveX component, a Java applet, or a C++ program.

12. The system of claim 1, comprising:
the first device to authenticate, prior to transmission of the indication of the modification to the set of objects, with a server for synchronizing with the set of objects stored in a server-side storage of the server.

13. The system of claim 1, wherein the first device is associated with a valid user identifier, and the second device is associated with the valid user identifier.

14. A method, comprising:
receiving, by a first application of a first device comprising one or more processors and memory, a modification to a set of objects;
transmitting, by the first device, via a network, an indication of the modification to the set of objects;
receiving, by a second device, the indication of the modification to the set of objects;
modifying, by the second device responsive to the indication, the set of objects stored on the second device;

receiving, by an input interface of the second device, a query;

presenting, by the second device through an output interface of the second device, in response to the query, a combined search results set generated via one or more search sub-processes, the combined search results set including at least two of:
 an object from the set of objects modified via the first device;
 an object from a first index; or
 an object from a second index.

15. The method of claim 14, comprising:
 transmitting, by the first device, the indication of the modification to a server; and
 receiving, by the second device, the indication of the modification to the set of objects from the server.

16. The method of claim 14, comprising:
 transmitting, by the first device, the indication of the modification to a server;
 synchronizing, by the server, the set of objects stored on the server based on the indication of the modification; and
 synchronizing, by the server, the set of objects with a plurality of other devices associated with the first device, the plurality of other devices comprising the second device.

17. The method of claim 14, comprising:
 modifying, by the first device responsive to receipt of the modification, the set of objects stored in a device-side storage on the first device.

18. The method of claim 14, wherein the modification to the set of objects received by the first device comprises an indication to create an object to add to the set of objects, comprising:
 adding, by the first device, the object to the set of objects in a device-side storage of the first device; and
 adding the object to the set of objects stored on a server.

19. The method of claim 14, wherein the set of objects comprises at least one of a set of bookmarks or a set of favorite items.

20. A non-transitory computer-readable medium storing instructions that, when executed by one or more processors, cause:
 a first processor to:
  receive a modification to a set of objects;
  transmit, via a network, an indication of the modification to the set of objects; a second processor to:
  receive the indication of the modification to the set of objects;
  modify, responsive to the indication, the set of objects stored in memory coupled to the second processor;
  receive a query;
  present, through an output interface coupled to the second processor, in response to the query, a combined search results set generated via one or more search sub-processes, the combined search results set including at least two of:
   an object from the set of objects modified via the interface of the first processor;
   an object from a first index; or
   an object from a second index.

* * * * *